United States Patent [19]

Kitahata et al.

[11] Patent Number: 5,523,218
[45] Date of Patent: Jun. 4, 1996

[54] METHOD OF PRODUCING A GALACTOSYL-CYCLODEXTRIN

[75] Inventors: Sumio Kitahata, 621-440, Noda, Kumatori-cho, Sennan-gun, Osaka; Koji Hara, Yokohama; Koki Fujita, Yokohama; Nobuhiro Kuwahara, Yokohama; Kyoko Koizumi, Fujiidera, all of Japan

[73] Assignees: Ensuiko Sugar Refining Co., Ltd., Yokohama; Sumio Kitahata, Osaka, both of Japan

[21] Appl. No.: 368,392

[22] Filed: Dec. 30, 1994

Related U.S. Application Data

[63] Continuation of Ser. No. 992,863, Dec. 17, 1992, abandoned.

[30] Foreign Application Priority Data

Apr. 8, 1992 [JP] Japan ................... 4-114304

[51] Int. Cl.$^6$ ............... C12P 19/04; C12P 19/44; C12P 19/18; C12P 19/08
[52] U.S. Cl. ............... 435/101; 435/74; 435/97; 435/103; 536/103
[58] Field of Search ............... 435/101, 74, 97, 435/103; 536/103

[56] References Cited

U.S. PATENT DOCUMENTS

| | | | |
|---|---|---|---|
| 4,668,626 | 5/1987 | Kobayashi et al. | 435/95 |
| 4,871,840 | 10/1989 | Kobayashi et al. | 536/103 |
| 4,910,137 | 3/1990 | Kobayashi et al. | 435/74 |
| 4,931,389 | 6/1990 | Kobayashi et al. | 435/95 |

FOREIGN PATENT DOCUMENTS

| | | |
|---|---|---|
| 541984 | 5/1993 | European Pat. Off. . |
| 3192101 | 8/1991 | Japan . |
| 5-43603 | 2/1993 | Japan . |
| 2165549 | 4/1986 | United Kingdom . |

OTHER PUBLICATIONS

Kitahata et al, "Galactosylation of Side Chains ..." Biosci, Biotech, Biochem. 56(2):pp. 242–245 (1992).
Kitahata et al, "Synthesis of 6-O-α-D-Galactosyl ..." Biosci, Biotech, Biochem. 56(9):pp. 1518–1519 (1992).
Lancelon-Pin et al "α-D-Mannosyl and β-D-Galactosyl Derivatives of Cyclodextrins", Tet. Letters 33(22):pp. 3125–3128 (1992).
Sigma Chemical Company Catalog, 1990, p. 499.
Patent Abstracts of Japan, unexamined applications, C field, vol. 16, No. 183, May 6, 1992, The Patent Office Japanese Government, p. 43 C 936, of JP 4–23,994.
Patent Abstracts of Japan, unexamined applications, C field, vol. 16, No. 180, Apr. 30, 1992, The Patent Office Japanese Government, p. 148 C 935, of JP 4–23,802.

*Primary Examiner*—John W. Rollins
*Assistant Examiner*—Francisco C. Prats
*Attorney, Agent, or Firm*—Frishauf, Holtz, Goodman, Langer & Chick

[57] ABSTRACT

Disclosed are (1) a novel galactosyl-cyclodextrin having a galactosyl group as bonded to the hydroxyl group of the glucosyl group of a cyclodextrin via an α-bond and a method of producing said galactosyl-cyclodextrin; (2) a novel galactosyl-cyclodextrin having a galactosyl group as bonded to the hydroxyl group of the glucosyl group of a cyclodextrin via a β-bond and a method of producing said galactosyl-cyclodextrin; and (3) a novel mannosyl-cyclodextrin having a mannosyl group as bonded to the hydroxyl group of the glucosyl group of a cyclodextrin via an α-bond and a method of producing said mannosyl-cyclodextrin. The new branched cyclodextrins are expected to be widely useful in various fields of drug industry, food industry and cosmetic industry.

5 Claims, 12 Drawing Sheets

(I)

(II)

(III)

(IV)

(V)

(VI)

(VII)

(VIII)

(IX)

G : Glucosyl Group
Gal : Galactosyl Group
Man : Mannosyl Group

Transfer Product

Mannose

α-CD

METHOD OF PRODUCING A GALACTOSYL-CYCLODEXTRIN

This application is a Continuation of application Ser. No. 07/992,863, filed Dec. 17, 1992, now abandoned.

FIELD OF THE INVENTION

The present invention relates to novel branched cyclodextrins and methods of preparing them and, more precisely, to a novel galactosylcyclodextrin having a galactosyl group bonded to the glucosyl group of a cyclodextrin by an α- or β-bond and a method of preparing the novel galactosyl-cyclodextrin by transgalactosylation of an enzyme and also to a novel mannosyl-cyclodextrin having a mannosyl group bonded to the glucosyl group of a cyclodextrin by an α-bond and a method of preparing the novel mannosyl-cyclodextrin by transmannosylation of an enzyme.

BACKGROUND OF THE INVENTION

A cyclodextrin (hereinafter referred to as "CD") is a cyclic dextrin composed of glucoses bonded to each other by an α-1,4 bond therebetween, and α-, β- and γ-CD each comprising 6, 7 and 8 glucoses, respectively, are well known. Recently, in order to elevate the solubility of CDs, branched CDs each having a glucosyl group or a maltosyl group bonded to CD via the α-1,6 bond have been produced.

Such CDs and branched CDs have cavities in the inside of the molecule and the inside of the cavities is lipophilic. Therefore, these CDs have an including capacity for forming inclusion (clathrate) compounds, taking various oily substances thereinto. As CDs and branched CDs have such properties, they are widely used in various fields of food industry, cosmetic industry and drug industry.

Recently, in the drug industry, in order to reduce the harmful side effects of drugs, a cell recognizing property of saccharides has been noticed and a study of utilizing CDs as a sensor to mark cells for a drug carrier in a drug delivery system has been effected actively. In particular, it is well known that galactose has a strong affinity with liver tissues and that mannose has an affinity with liver parenchymatous cells, liver non-parenchymatous cells and macrophages.

We the present inventors have already succeeded in development of a galactosyl-branched CD and a mannosyl-branched CD in which a galactosyl group or a mannosyl group, respectively, is bonded to the glucosyl group of the side chain of a branched cyclodextrin.

Under the situation, we tried to produce a galactosyl-CD and a mannosyl-CD in which a galactosyl group or a mannosyl group, respectively, is directly bonded to the CD ring by transglycosylation, for the purpose of applying both the including capacity of CDs and the above-mentioned characteristics of galactose and mannose to a drug delivery system. As a result, we have found that a commercial α-galactosidase is used for producing a galactosyl-CD in which a galactosyl group is bonded to the glucosyl group of an α-, β- or γ-CD via an α-bond by transgalactosylation from an α-galactosyl compound, that a commercial β-galactosidase is used for producing a galactosyl-CD in which a galactosyl group is bonded to the glucosyl group of an α-, β- or γ-CD via a β-bond by transgalactosylation, from a β-galactosyl compound, and that a commercial α-mannosidase is used for producing a mannosyl-CD in which a mannosyl group is bonded to the glucosyl group of an α-, β- or γ-CD via an α-bond by transmannosylation, from an α-mannosyl compound. In particular, we have found that an α-galactosidase derived from green coffee beans is used for efficiently producing a galactosyl-CD in which one or two galactosyl groups are bonded to the glucosyl group of an α-, β- or γ-CD via an α-1,6 bond by transgalactosylation. In addition, we also have found that an α-mannosidase derived from jack beans is used for efficiently producing a mannosyl-CD in which one mannosyl group is bonded to the glucosyl group of an α-, β- or γ-CD via an α-1,6 bond by transmannosylation. On the basis of the finding, we have completed the present invention.

SUMMARY OF THE INVENTION

Specifically, the present invention provides a novel galactosyl-CD having a galactosyl group as bonded to the 6-hydroxyl group of the glucosyl group of a CD via an α- or β-bond; and also provides a method of producing a novel galactosyl-CD having a galactosyl group bonded to the 6-hydroxyl group of the glucosyl group of a CD via an α-bond, in which a liquid containing a CD and an α-galactosyl compound is treated with an α-galactosyl transfer enzyme, as well as a method of producing a novel galactosyl-CD having a galactosyl group bonded to the 6-hydroxyl group of the glucosyl group of a CD via a β-bond, in which a liquid containing a CD and a β-galactosyl compound is treated with a β-galactosyl transfer enzyme. It further provides a novel mannosyl-CD having a mannosyl group as bonded to the 6-hydroxyl group of the glucosyl group of a CD via an α-bond as well as a method of producing a novel mannosyl-CD having a mannosyl group bonded to the 6-hydroxyl group of the glucosyl group of a CD via an α-bond, in which a liquid containing a CD and an α-mannosyl compound is treated with an α-mannosyl transfer enzyme.

DETAILED DESCRIPTION OF THE INVENTION

Figure 1:
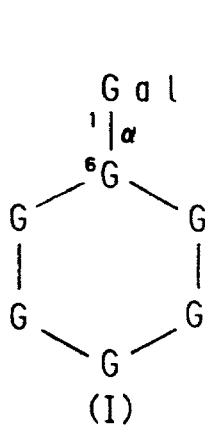
FIG. 1 shows structures of branched CDs to be obtained by the present invention.
Figure 1:
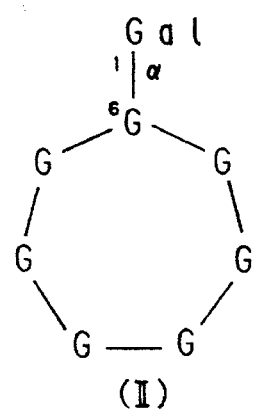
Figure 1:
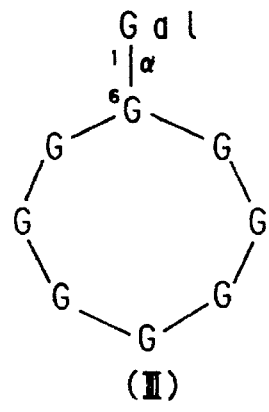
Figure 1:
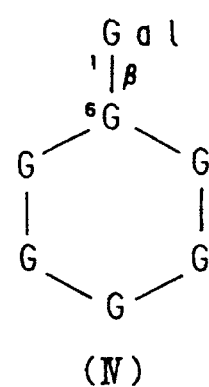
Figure 1:
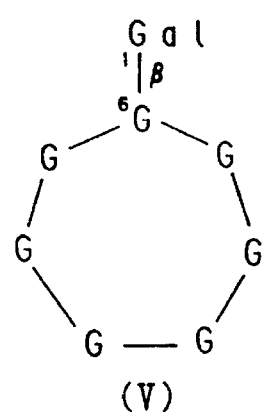
Figure 1:
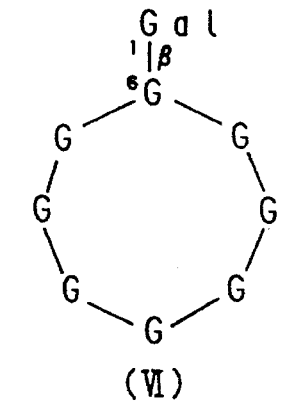
Figure 1:
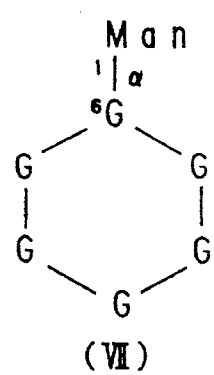
Figure 1:
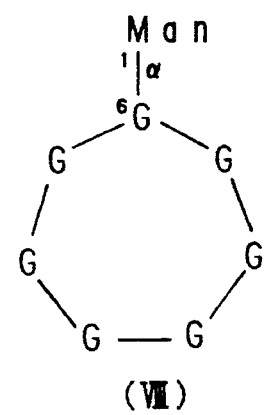
Figure 1:
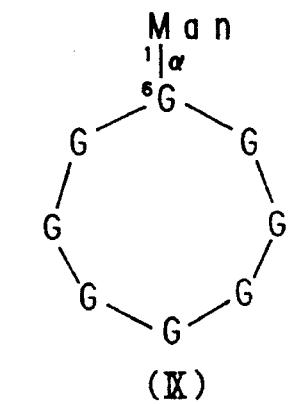

New branched CDs of the present invention are represented by structural formulae I to IX as shown in FIG. 1.

New branched CDs of the present invention can be obtained by treating a liquid containing a CD and an α-galactosyl compound with an α-galactosyl transfer enzyme, or by treating a liquid containing a CD and a β-galactosyl compound with a β-galactosyl transfer enzyme, or by treating a liquid containing a CD and an α-mannosyl compound with an α-mannosyl transfer enzyme.

In the present invention, CD may be any of α-, β- and γ-CDs or branched CDs each having a glucosyl group or maltosyl group or may also be a mixture of them.

As the α-galactosyl compound for use in the present invention (hereinafter referred to as "glycosyl donor 1"), there are mentioned for example, α-galactosyl residue containing glycosides, oligosaccharides and polysaccharides, such as melibiose, phenyl α-galactoside, paranitrophenyl α-galactoside and α-gatactooligosaccharides, as well as partially decomposed products of them and mixtures of them.

The β-galactosyl compound for use in the present invention (hereinafter referred to as "glycosyl donor 2") includes, for example, β-galactosyl residue-containing glycosides, oligosaccharides and polysaccharides, such as lactose, phenyl β-galactoside, paranitrophenyl β-galactoside and β-galactooligosaccharides, as well as partially decomposed products of them and mixtures of them.

The α-mannosyl compound for use in the present invention (hereinafter referred to as "glycosyl donor 3") includes, for example, α-mannosyl residue-containing glycosides, oligosaccharides and polysaccharides, such as methyl α-mannoside, phenyl α-mannoside, paranitrophenyl α-mannoside and α-mannooligosaccharides, as well as partially decomposed products of them and mixtures of them.

As the α-galactosyl transfer enzyme for the present invention, anyone may be used which reacts with a liquid containing an α-galactosyl compound and a CD to decompose the glycosyl donor 1 to thereby transfer the α-galactosyl group to the CD by an α-bond to give an α-galactosyl-CD. In the same manner, as the β-galactosyl transfer enzyme for the present invention, anyone may be used which reacts with a liquid containing a β-galactosyl compound and a CD to decompose the glycosyl donor 2 to thereby transfer the β-galactosyl group to the CD by a β-bond to give a β-galactosyl-CD; and as the α-mannosyl transfer enzyme for the present invention, anyone may be used which reacts with a liquid containing an α-mannosyl compound and a CD to decompose the glycosyl donor 3 to thereby transfer the α-mannosyl group to the CD by an α-bond to give an α-mannosyl-CD.

The α-galactosyl transfer enzyme to be used in the present invention is selected from those which are widely distributed in the natural field. For instance, well known are enzymes derived from plants such as green coffee beans and enzymes derived from microorganisms such as *Aspergillus nigear, Escherichia coli* and *Mortiellera vinasce*. The β-galactosyl transfer enzyme for use in the present invention may be also selected from those which are widely distributed in the natural field. For instance, well known are those derived from microorganisms such as *Aspergillus nigear, Aspergillus oryzae* and *Penicillium multicolor.*

The α-mannosyl transfer enzyme for use in the present invention is also selected from those which are widely distributed in the natural field. For instance, well known are enzymes derived form plants such as jack beans or almond, enzymes derived from animals such as turbos or livers (bovine, rat, human), and enzymes derived from microorganisms such as *Arthrobacter aurescens* and *Aspergillus nigear.*

In the reaction system of the present invention, the liquid (aqueous solution or suspension) containing a CD and a glycosyl donor is desired to have a CD concentration of approximately from 1 to 50% (w/w) and a glycosyl donor concentration of approximately from 1 to 90% (w/w). The proportion (by weight) of glycosyl donor to CD is, though varying in accordance with the kind of the glycosyl donor to be used, suitably within the range of from 0.1/1 to 50/1, preferably from 0.3/1 to 2/1.

In carrying out the reaction of the present invention, the pH value of the reaction mixture may be from 3 to 10, preferably from 4 to 9; and the temperature thereof may be from 20° to 70° C., preferably from 30° to 60° C. The amount of the enzyme to be used in the reaction and the reaction time are closely related to each other. In general, the former may be such that the reaction may be finished in 5 to 100 hours, preferably in 5 to 20 hours, which, however, is not limitative.

The reaction mixture as obtained by the reaction method mentioned above is subjected to high performance liquid chromatography (HPLC), whereupon the transfer product of CD is fractionated and isolated. Next, the structure of the product thus obtained is analyzed by enzymatic decomposition, molecular weight measurement by FAB-MB and nuclear magnetic resonance (NMR). As a result, the product has been identified to be a branched CD as represented by anyone of formulae I to IX of FIG. 1.

The present invention will be explained in more detail by way of the following examples, which, however, are not intended to restrict the scope of the present invention.

EXAMPLE 1

(1) Transfer Reaction

Figure 2:
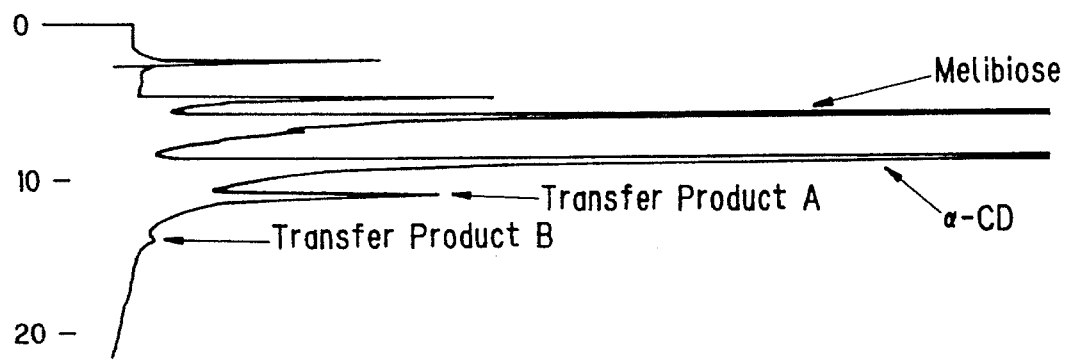
FIG. 2 shows a high performance liquid chromatograph of the reaction mixture of Example 1.

Six hundred mg of melibiose and 600 mg of α-CD were dissolved in 1.5 ml of 50 mM acetate acid buffer (pH 6.5), and 9 units of green coffee beans α-galactosidase (produced by Sigma Co.) were added thereto and reacted at 40° C. for 17 hours. A part of the reaction mixture was analyzed by high performance liquid chromatography, and the analyzed result is shown in FIG. 2.

After the reaction, the reaction mixture in which the enzyme used was inactivated under heat was subjected to high performance liquid chromatography to isolate 85 mg of a transfer product A.

(2) Analysis of Structure

Figure 3:
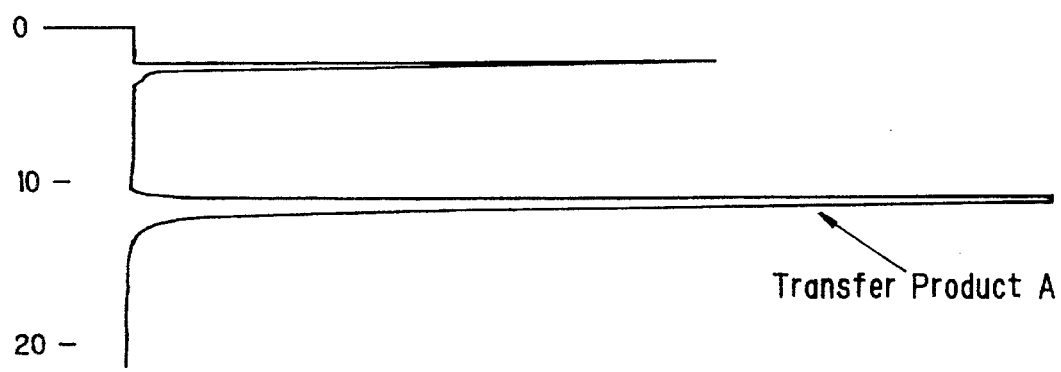
FIG. 3 shows a high performance liquid chromatograph of the transfer product A of Example 1.
Figure 4:
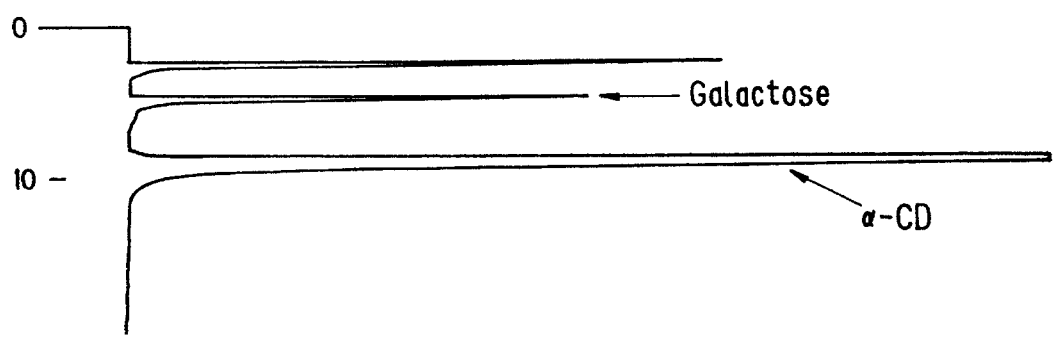
FIG. 4 shows a high performance liquid chromatograph of hydrolyzates of the transfer product A of Example 1.
Figure 5:
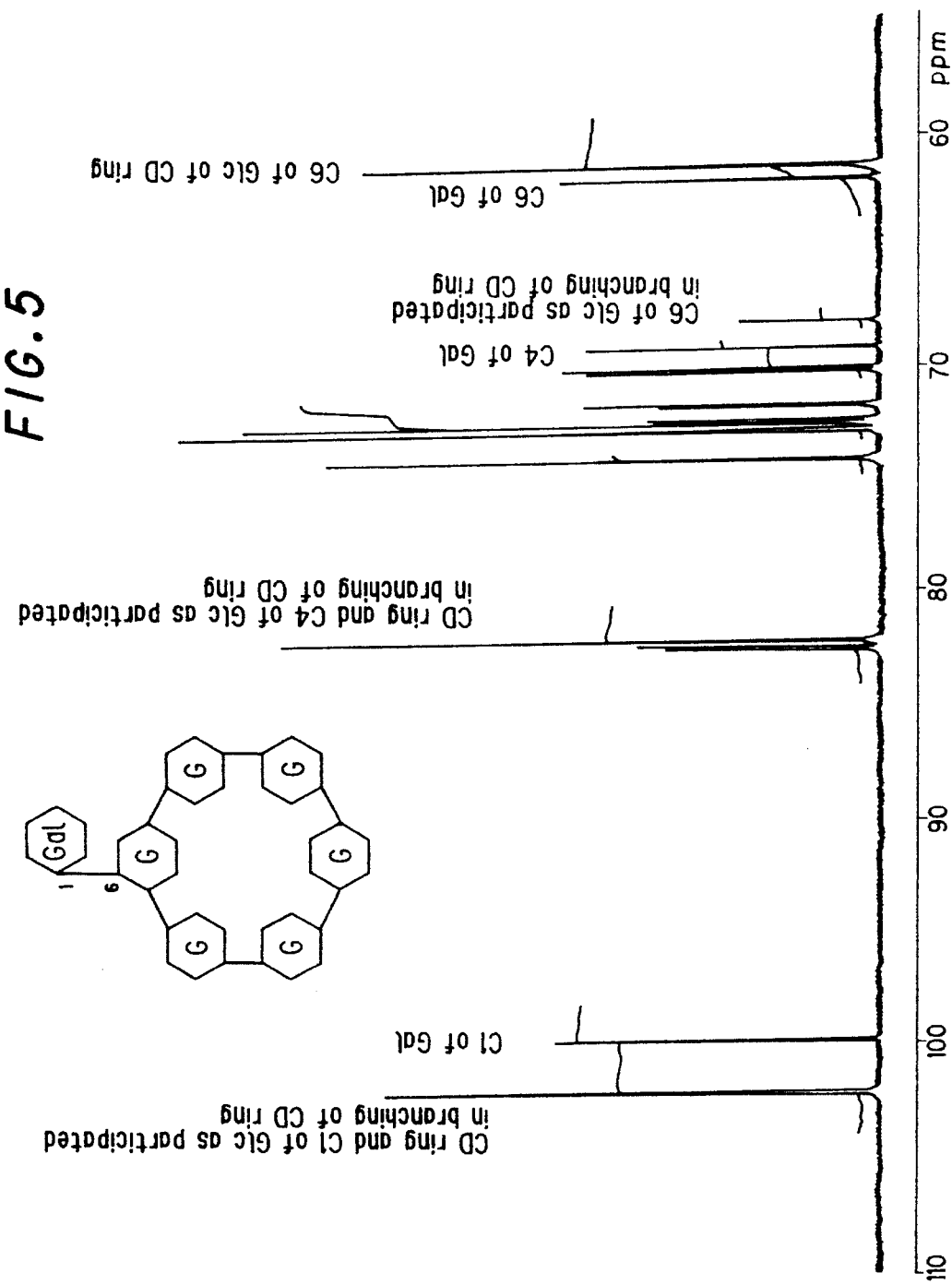
FIG. 5 shows a $^{13}$C-NMR analysis spectrum of the transfer product A of Example 1.

The transfer product A (FIG. 3) as isolated in the above-mentioned step (1) was identified to have a molecular weight of 1134 by FAB-MS analysis. As shown in FIG. 4, it was completely hydrolyzed into galactose and α-CD of the same molar amounts by green coffee beans α-galactosidase. By $^{13}$-NMR analysis, the product was identified to be a compound having a galactosyl group as bonded to the 6-hydroxyl group of the glucosyl group of α-CD via an α-bond (structural formula I of FIG. 1), as shown in FIG. 5.

In the same manner, the transfer product B as isolated in the above-mentioned step (1) was completely hydrolyzed by green coffee beans α-galactosidase to form α-CD and two molar times of galactose. From this, the transfer product B was presumed to be a compound having two molecules of galactosyl group as bonded to the 6-hydroxyl group of the glucosyl group of α-CD via an α-bond.

EXAMPLE 2

(1) Transfer Reaction

Figure 6:
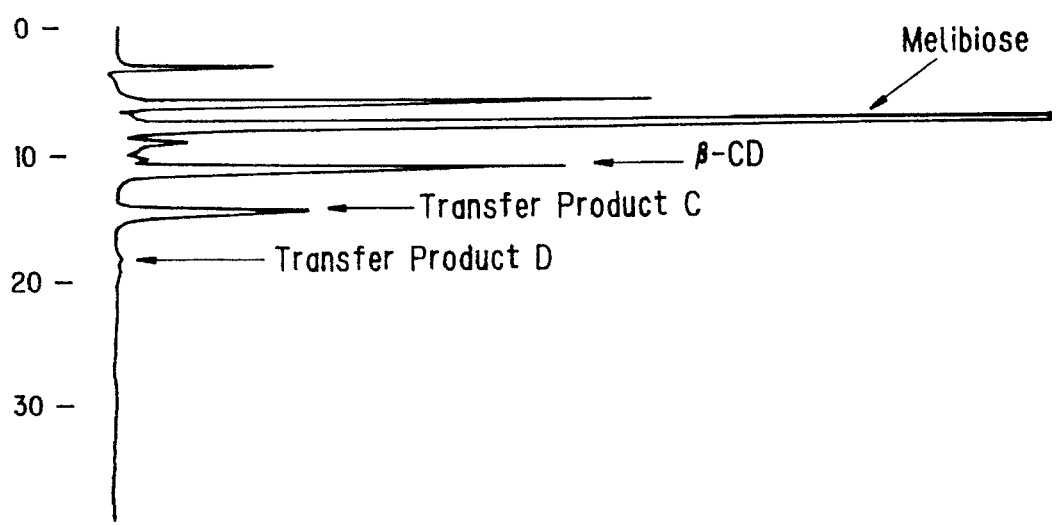
FIG. 6 shows a high performance liquid chromatograph of the reaction mixture of Example 2.

Six hundred mg of melibiose and 300 mg of β-CD were dissolved in 1.5 ml of 50 mM acetate acid buffer (pH 6.5), and 9 units of green coffee beans α-galactosidase transferase (produced by Sigma Co.) were added thereto and reacted at 40° C. for 17 hours. A part of the reaction mixture was analyzed by high performance liquid chromatography, and the analyzed result is shown in FIG. 6.

After the reaction, the reaction liquid in which the enzyme used was inactivated under heat was subjected to high performance liquid chromatography to isolate 66 mg of a transfer product C.

Figure 7:
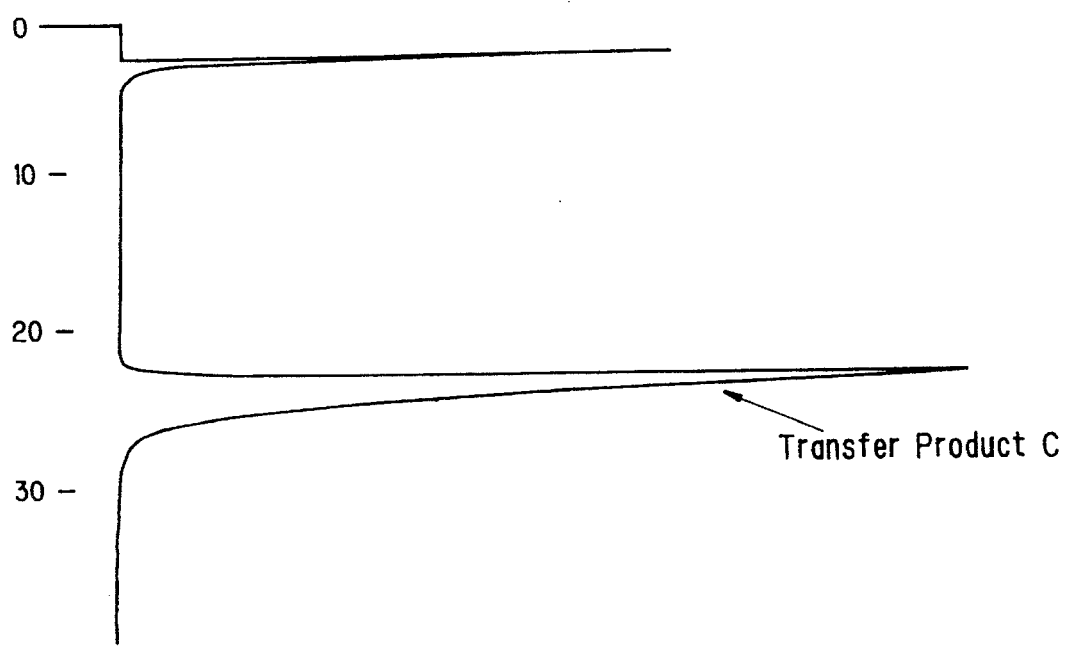
FIG. 7 shows a high performance liquid chromatograph of the transfer product C of Example 2.
Figure 8:
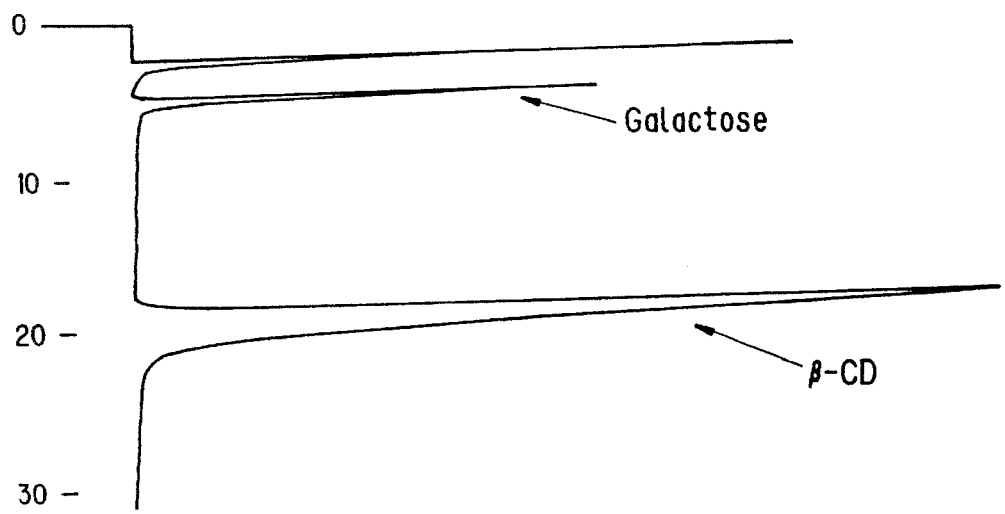
FIG. 8 shows a high performance liquid chromatograph of hydrolyzates of the transfer product C of Example 2.
Figure 9:
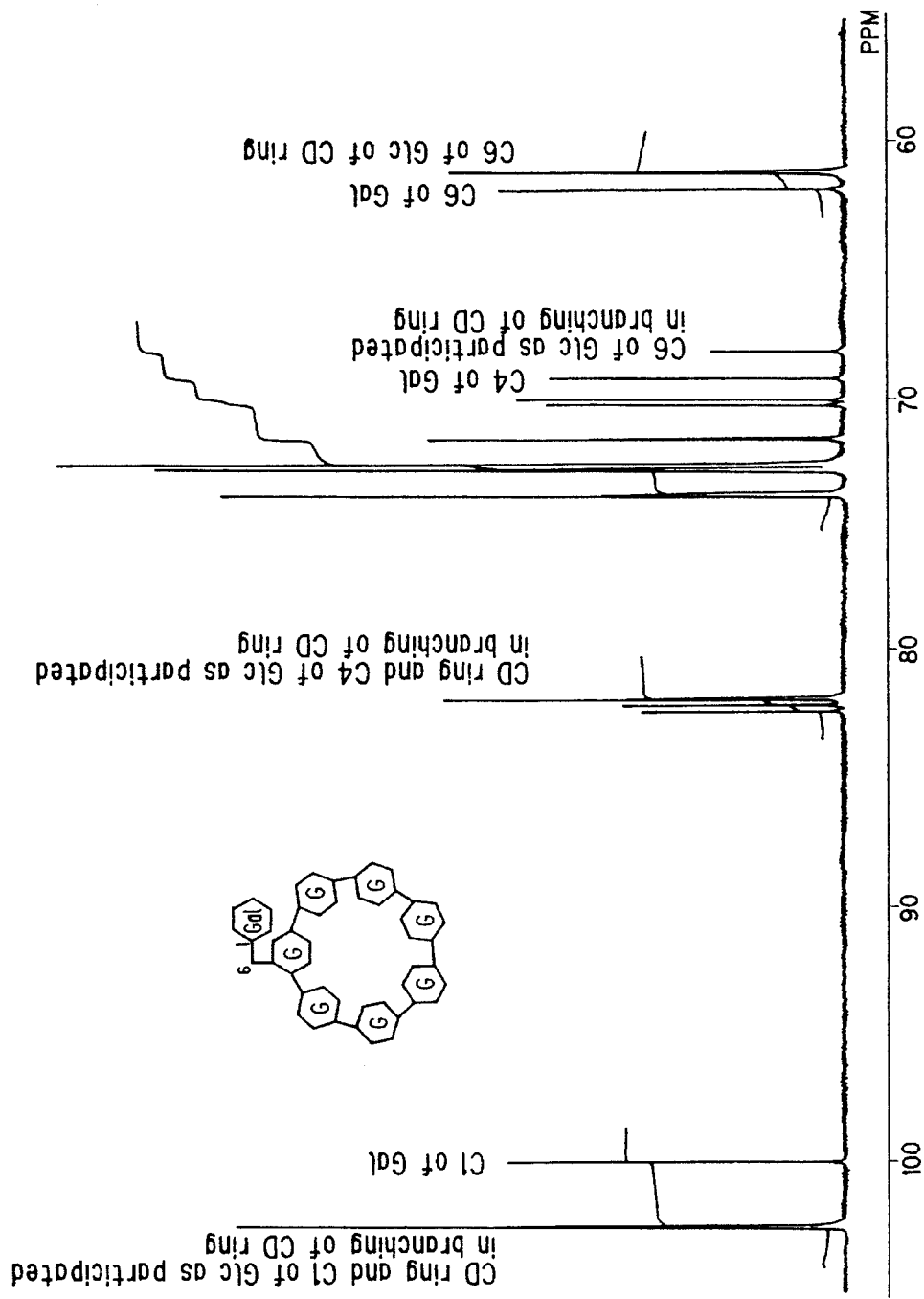
FIG. 9 shows a $^{13}$C-NMR analysis spectrum of the transfer product A of Example 2.

(2) Analysis of Structure:

The transfer product C (FIG. 7) as isolated in the above-mentioned step (1) was identified to have a molecular weight of 1296 by FAB-MS analysis. As shown in FIG. 8, it was completely hydrolyzed into galactose and β-CD of the same molar amounts by green coffee beans α-galactosidase. Further, $^{13}$C-NMR analysis of the transfer product C was shown in FIG. 9. From these results, the transfer product was identified to be a compound having a galactosyl group as bonded to the 6-hydroxyl group of the glucosyl group of β-CD via an α-bond (structural formula II of FIG. 1).

In the same manner, the transfer product D as isolated in the above-mentioned step (1) was completely hydrolyzed by green coffee beans α-galactosidase to form β-CD and two molar times of galactose. From this, the transfer product D was presumed to be a compound having two molecules of galactosyl group as bonded to the 6-hydroxyl group of the glucosyl group of β-CD via an α-bond.

EXAMPLE 3

Figure 10:
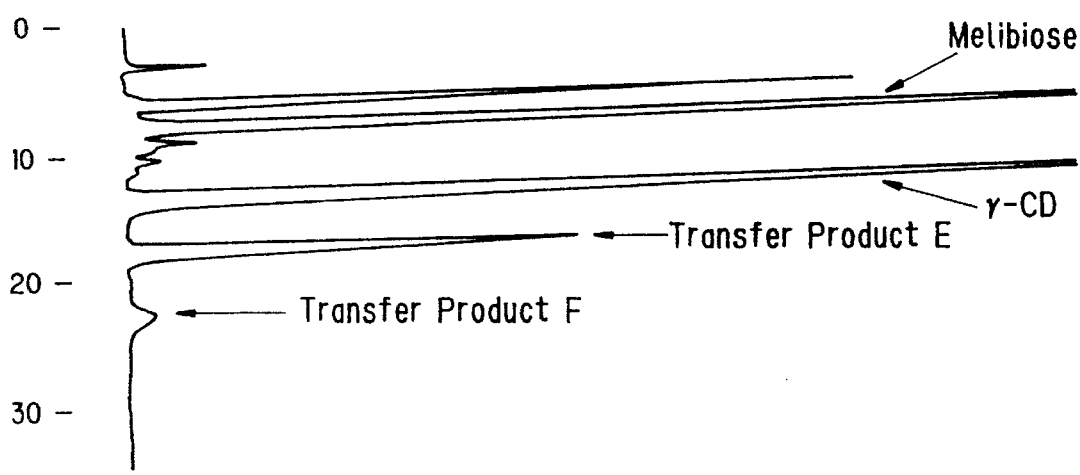
FIG. 10 shows a high performance liquid chromatograph of the reaction mixture of Example 3.

(1) Transfer Reaction:

Six hundred mg of melibiose and 600 mg of γ-CD were dissolved in 1.5 ml of 50 mM acetate buffer (pH 6.5), and 9 units of green coffee beans α-galactosidase transferase (produced by Sigma Co.) were added thereto and reacted at 40° C. for 17 hours. A part of the reaction mixture was analyzed by high performance liquid chromatography, and the analyzed result is shown in FIG. 10.

After the reaction, the reaction liquid in which the enzyme used was inactivated under heat was subjected to high performance liquid chromatography to isolate 93 mg of a transfer product E.

Figure 11:
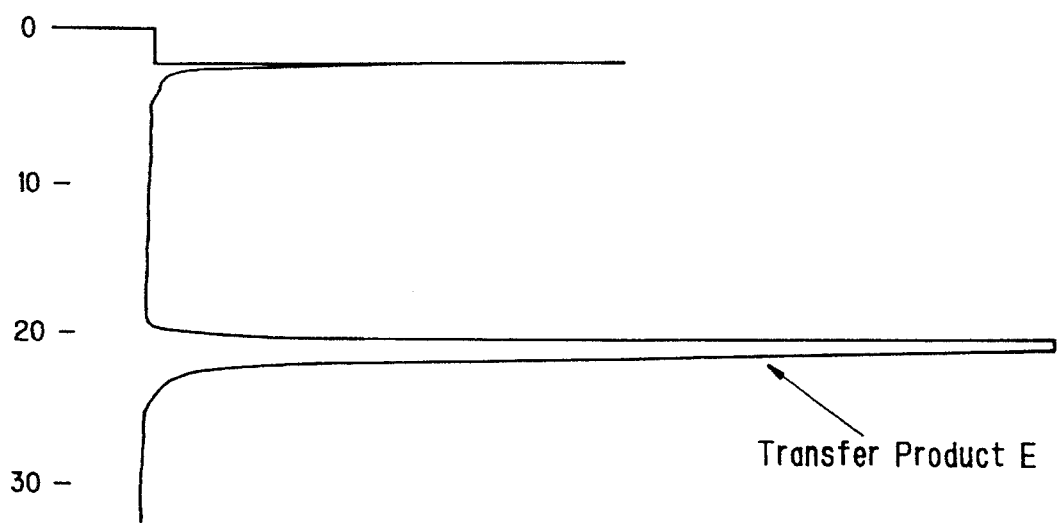
FIG. 11 shows a high performance liquid chromatograph of the transfer product E of Example 3.
Figure 12:
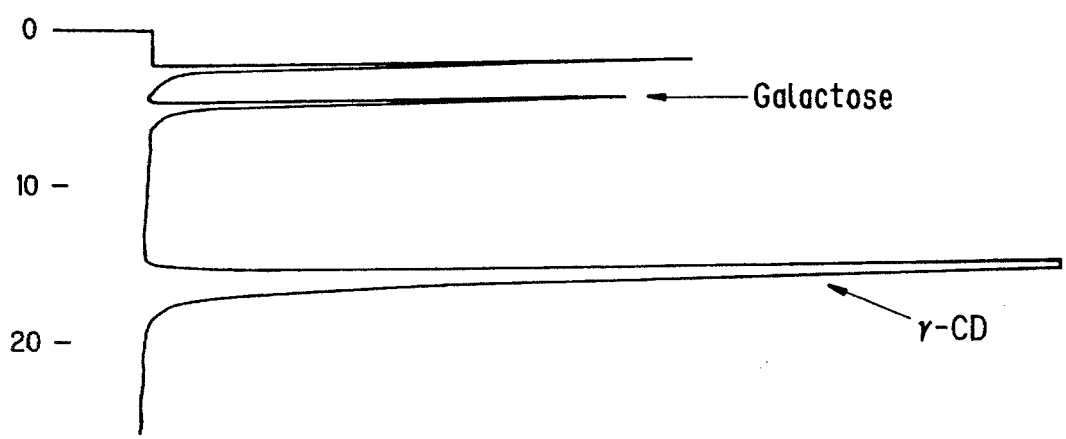
FIG. 12 shows a high performance liquid chromatograph of hydrolyzates of the transfer product E of Example 3.
Figure 13:
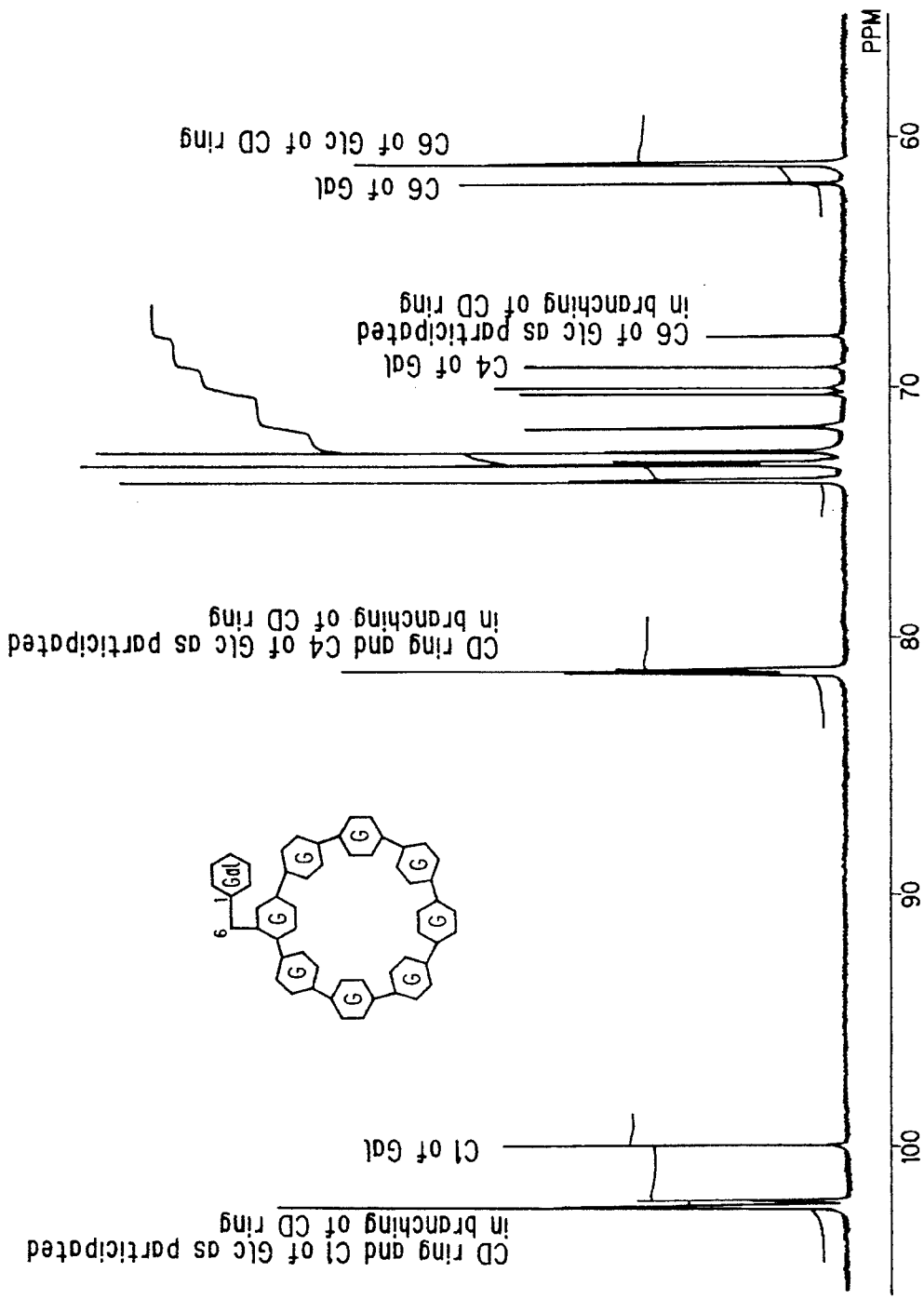
FIG. 13 shows a $^{13}$C-NMR analysis spectrum of the transfer product A of Example 3.

(2) Analysis of Structure:

The transfer product E (FIG. 11) as isolated in the above-mentioned step (1) was identified to have a molecular weight of 1458 by FAB-MS analysis. As shown in FIG. 12, it was completely hydrolyzed into galactose and γ-CD of the same molar amounts by green coffee beans α-galactosidase. Further, $^{13}$C-NMR analysis of the transfer product E was shown in FIG. 13. From these results, the transfer product was identified to be a compound having a galactosyl group as bonded to the 6-hydroxyl group of the glucosyl group of γ-CD via an α-bond (structural formula III of FIG. 1).

In the same manner, the transfer product F as isolated in the above-mentioned step (1) was completely hydrolyzed by green coffee beans α-galactosidase to form γ-CD and two molar times of galactose. From this, the transfer product F was presumed to be a compound having two molecules of galactosyl group as bonded to the 6-hydroxyl group of the glucosyl group of γ-CD via an α-bond.

EXAMPLE 4

(1) Transfer Reaction

Two g of lactose and 2 g of α-CD were dissolved in 3 ml of 50 mM acetate buffer (pH 4.5), and 40 units of *Penicillium multicolor* β-galactosidase (produced by KI Chemicals Co., Japan) were added thereto and reacted at 40° C. for 4 hours. For comparison, only lactose was treated with the same enzyme in the absence of CD.

Figure 14:
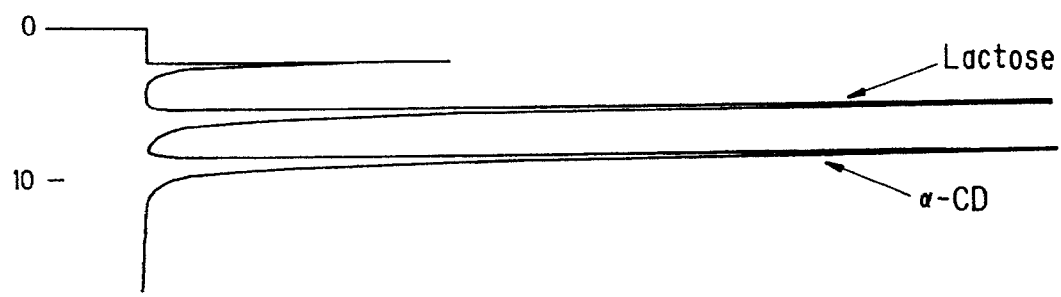
FIG. 14 shows a high performance liquid chromatograph of the reaction mixture (reaction time: 0 minute) of Example 4.
Figure 15:
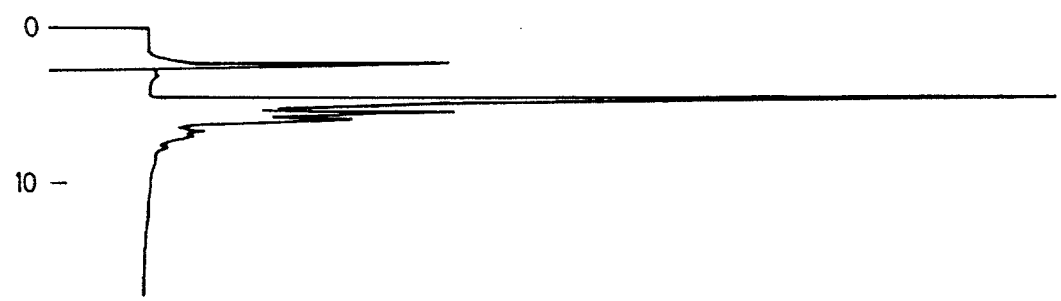
FIG. 15 shows a high performance liquid chromatograph of the reaction mixture (lactose only) of Example 4.
Figure 16:
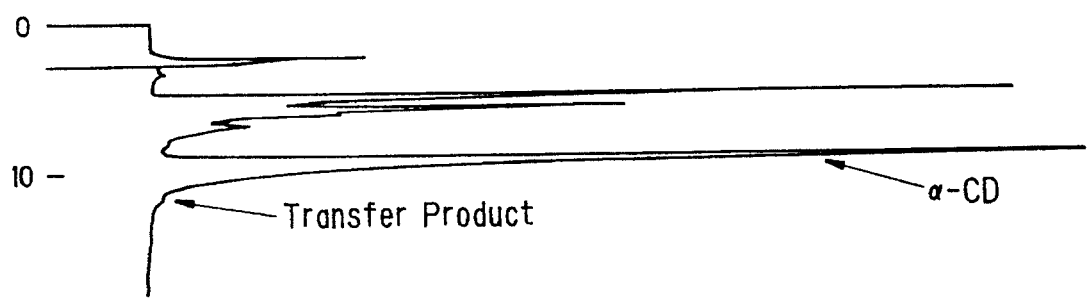
FIG. 16 shows a high performance liquid chromatograph of the reaction mixture (reaction time: 4 hours) of Example 4.

A part of the reaction mixture was analyzed by high performance liquid chromatography, and the analyzed results are shown in FIG. 14 to FIG. 16. FIG. 14 indicates the result of reaction for 0 (zero) minute between enzyme and lactose along with α-CD. FIG. 15 indicates the result of reaction for 4 hours between enzyme and only lactose in the absence of α-CD. FIG. 16 indicates the result of reaction for 4 hours between enzyme and lactose along with α-CD.

After the reaction, the reaction liquid in which the enzyme used was inactivated under heat was subjected to high performance liquid chromatography to isolate 10 mg of a transfer product.

(2) Analysis of Structure

Figure 17:
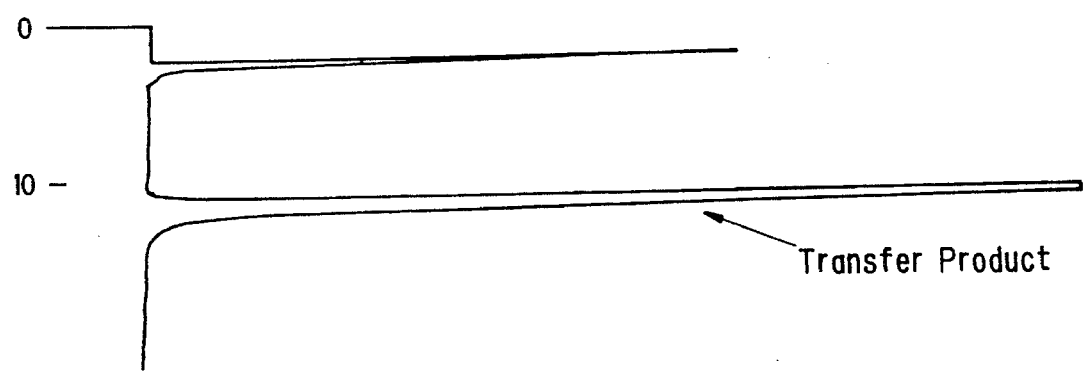
FIG. 17 shows a high performance liquid chromatograph of the transfer product of Example 4.
Figure 18:
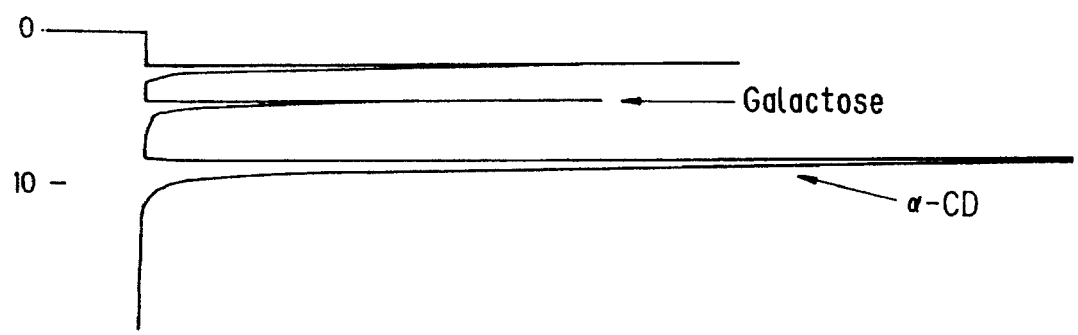
FIG. 18 shows a high performance liquid chromatograph of hydrolyzates of the transfer product of Example 4.

The transfer product (FIG. 17) as isolated in the above-mentioned step (1) was identified to have a molecular weight of 1134 by FAB-MS analysis. As shown in FIG. 18, it was completely hydrolyzed into galactose and α-CD of the same molar amounts by Penicillium multicolor β-galactosidase. The galactosyl-transfer position to maltosyl-α-CD by the present enzyme was already reported to be the 6-hydroxyl group of the glucosyl group of the side chain (Japanese Patent Kokai 4-23802).

From the above results, the transfer product was identified to be a compound having a galactosyl group as bonded to the 6-hydroxyl group of the glucosyl group of α-CD via a β-bond (structural formula IV of FIG. 1).

EXAMPLE 5

(1) Transfer Reaction

Figure 19:
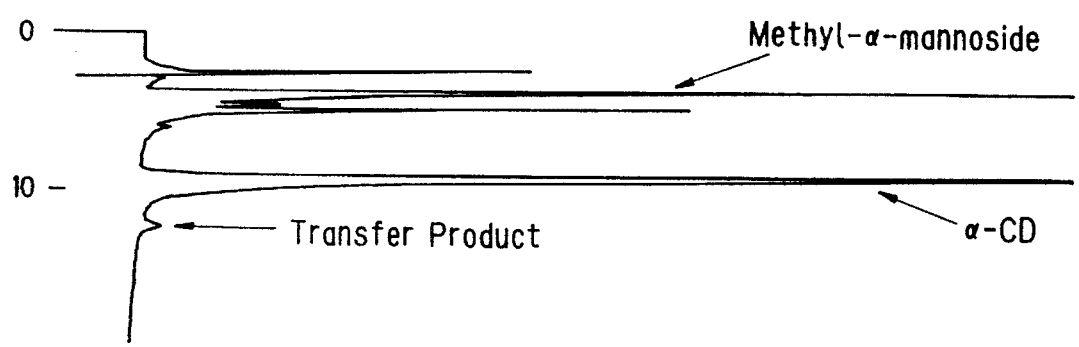
FIG. 19 shows a high performance liquid chromatograph of the reaction mixture of Example 5.

Three g of methyl α-mannoside and 3 g of α-CD were dissolved in 10 ml of 50 mM acetate buffer (pH 4.5), and 51 units of jack beans α-mannosidase (produced by Sigma Co.) were added thereto and reacted at 40° C. for 24 hours. A part of the reaction mixture was analyzed by high performance liquid chromatography, and the analyzed result is shown in FIG. 19.

After the reaction, the reaction mixture in which the enzyme used was inactivated under heat was subjected to high performance liquid chromatography to isolate 73 mg of a transfer product.

Figure 20:
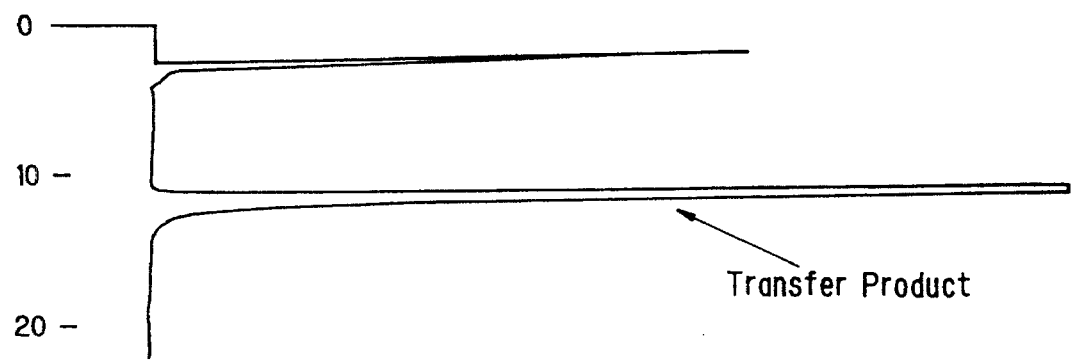
FIG. 20 shows a high performance liquid chromatograph of the transfer product of Example 5.
Figure 21:
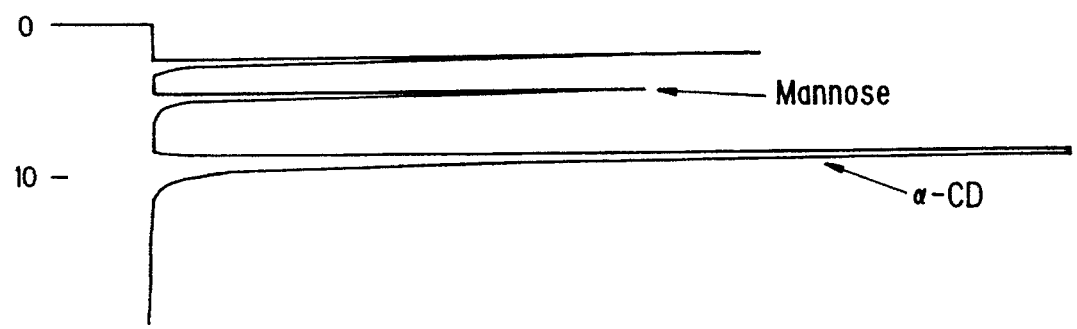
FIG. 21 shows a high performance liquid chromatograph of hydrolyzates of the transfer product of Example 5.

(2) Analysis of Structure:

The transfer product (FIG. 20) as isolated in the above-mentioned step (1) was identified to have a molecular weight of 1134 by FAB-MS analysis. As shown in FIG. 21, it was completely hydrolyzed into mannose and α-CD of the same molar amounts by jack beans α-mannosidase. The mannosyl-transfer position to glucosyl-α-CD by the present enzyme was already known to be the 6-hydroxyl group of the glucosyl group of the side chain (Japanese Patent Application No. 3-324021). Therefore, regarding the structure of the transfer product, it was identified to be a compound having a mannosyl group as bonded to the 6-hydroxyl group of the glucosyl group of α-CD via an α-bond (structural formula VII of FIG. 1).

In accordance with the present invention, as has been explained in detail in the above, a novel branched CD having a galactosyl group as bonded to the hydroxyl group of the glucosyl group in the CD molecule via an α-1,6 bond is obtained efficiently by transgalactosylation of an ∇-galactosyl transfer enzyme. Also, a novel branched CD having a galactosyl group as bonded to the hydroxyl group of the glucosyl group in the CD molecule via a β-1,6 bond is obtained efficiently by transgalactosylation of a β-galactosyl transfer enzyme. Further, a novel branched CD having a mannosyl group as bonded to the hydroxyl group of the glucosyl group in the CD molecule via an α-1,6 bond is also obtained efficiently by transmannosylation of an α-mannosyl transfer enzyme.

The new branched CDs of the present invention are expected to be widely used in various fields of drug industry, food industry and cosmetic industry.

While the invention has been described in detail and with reference to specific embodiments thereof, it will be apparent to one skilled in the art that various changes and modifications can be made therein without departing from the spirit and scope thereof.

What is claimed is:

1. A method of producing a galactosylcyclodextrin having one or two molecules of a galactosyl group bonded to a 6-hydroxyl group of a glucosyl group of a cyclodextrin via an α-bond, which comprises (a) treating a liquid containing a cyclodextrin and an α-galactosyl compound selected from the group consisting of melibiose, phenyl α-galactoside, paranitrophenyl α-galactoside and α-galactooligosaccharide with a green coffee bean α-galactosyl transfer enzyme at a pH of 3 to 10 and a temperature of 20° to 70° C. to form a reaction mixture and (b) recovering the galactosyl-cyclodextrin from the reaction mixture.

2. The method as claimed in claim 1, wherein the liquid contains 1 to 50% (w/w) of cyclodextrin and 1 to 90% (w/w) of the α-galactosyl compound.

3. The method as claimed in claim 1, wherein the pH is 4 to 9, the temperature is 30° to 60° C. and the method is carried out for 5 to 100 hours.

4. The method as claimed in claim 2, wherein the pH is 4 to 9, and the temperature is 30 to 60° C. and the method is carried out for 5 to 100 hours.

5. The method as claimed in claim 1, wherein the reaction mixture from step (a) is subjected to high performance liquid chromatography to recover the galactosyl-cyclodextrin in step (b).

* * * * *